United States Patent
Saito et al.

(10) Patent No.: US 9,290,804 B2
(45) Date of Patent: Mar. 22, 2016

(54) MICROPARTICLE HAVING SINGLE-MOLECULE NUCLEIC ACID PROBE, METHOD FOR PRODUCING SAME, METHOD FOR ANALYZING NUCLEIC ACID USING SAME, DEVICE FOR NUCLEIC ACID ANALYSIS, AND APPARATUS FOR ANALYZING NUCLEIC ACID

(75) Inventors: Toshiro Saito, Hitachinaka (JP); Kazumichi Imai, Hitachinaka (JP); Takayuki Obara, Tsuchiura (JP); Eri Tarasawa, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 42 days.

(21) Appl. No.: 13/981,983

(22) PCT Filed: Jan. 26, 2012

(86) PCT No.: PCT/JP2012/051636
§ 371 (c)(1),
(2), (4) Date: Jul. 26, 2013

(87) PCT Pub. No.: WO2012/102329
PCT Pub. Date: Aug. 2, 2012

(65) Prior Publication Data
US 2013/0309675 A1 Nov. 21, 2013

(30) Foreign Application Priority Data

Jan. 26, 2011 (JP) .................................. 2011-013554
Mar. 30, 2011 (JP) .................................. 2011-074849

(51) Int. Cl.
C12Q 1/68 (2006.01)
C12P 19/34 (2006.01)

(52) U.S. Cl.
CPC ............ *C12Q 1/6869* (2013.01); *C12Q 1/6806* (2013.01); *C12Q 1/6834* (2013.01); *C12Q 1/6876* (2013.01)

(58) Field of Classification Search
None
See application file for complete search history.

(56) References Cited

U.S. PATENT DOCUMENTS

| 2003/0064400 A1 | 4/2003 | William |
| 2005/0250117 A1 | 11/2005 | Su et al. |
| 2006/0068409 A1* | 3/2006 | Phan et al. ................ 435/6 |
| 2010/0009862 A1 | 1/2010 | Nakahara et al. |

FOREIGN PATENT DOCUMENTS

| JP | 2002-58495 | 2/2002 |
| JP | 2008-190937 | 8/2008 |
| JP | 2009-85840 | 4/2009 |

OTHER PUBLICATIONS

Michael R. Stratton et al., The cancer genome, Nature, Apr. 9, 2009, pp. 719-724, vol. 458.
Genome-wide association study of 14,000 cases of seven common diseases and 3,000 shared controls, Nature, Jun. 7, 2007, pp. 661-678, vol. 447, The Wellcome Trust Case Control Consortium.
Edwin H. Cook Jr. et al, Copy-number variations associated with neuropsychiatric conditions, Nature, Oct. 16, 2008, pp. 919-923, vol. 455.
P Bharadwaj et al., Nanoplasmonic enhancement of single-molecule fluorescence, Nanotechnology 18 (2007).
Anton Valouev et al., A high-resolution, nucleosome position map of C. elegans reveals a lack of universal sequence-dictated positioning, Genome Res. 18: 1051 (2008).
Jingyue Ju et al., Four-color DNA sequencing by synthesis using cleavable fluorescent nucleotide reversible terminators, PNAS, Dec. 26, 2006, pp. 19635-19640, vol. 103, No. 52.

* cited by examiner

*Primary Examiner* — James Martinell
(74) *Attorney, Agent, or Firm* — Baker Botts L.L.P.

(57) ABSTRACT

A microparticle having a probe molecule able to capture a specific nucleic acid group to be analyzed is used to extract only the specific nucleic acid group to be analyzed from a nucleic acid sample and the microparticle is thereafter directly immobilized on a smooth plate, whereby a device for nucleic acid analysis is rapidly prepared. Immobilizing a single capture probe molecule onto an individual microparticle in advance and forming, at regular positions on the smooth substrate, an adhesion pad on which a functional group that binds to the microparticle has been introduced makes it possible to readily and rapidly prepare the device for nucleic analysis, where the nucleic acid sample to be analyzed is arranged molecule by molecule in a lattice shape on the smooth substrate.

5 Claims, 9 Drawing Sheets

(a)

(b)

MICROPARTICLE HAVING SINGLE-MOLECULE NUCLEIC ACID PROBE, METHOD FOR PRODUCING SAME, METHOD FOR ANALYZING NUCLEIC ACID USING SAME, DEVICE FOR NUCLEIC ACID ANALYSIS, AND APPARATUS FOR ANALYZING NUCLEIC ACID

TECHNICAL FIELD

The present invention relates to a single-molecule probe nucleic acid-loaded microparticle, a preparation process thereof, and a nucleic acid analysis method, nucleic acid analysis device, and nucleic acid analyzer using the microparticle.

BACKGROUND ART

In recent years, a method of immobilizing a number of nucleic acid fragment samples on a smooth substrate and thereby determining the sequence information of these fragments in parallel has been developed and being industrialized.

Analysis using, as a nucleic acid sample to be analyzed, whole genome DNA, whole RNA, or cDNA library which is a reverse transcription product of messenger RNA has been conducted popularly. On the other hand, an analysis method with only a specific site of genome DNA or RNA is widening from the standpoint of saving the cost and time for analysis. In addition, superiority of sequence analysis with an accuracy of even one base has been recognized by narrowing a region on a disease-related gene group or genome and instead of it, increasing redundancy of sequence analysis. For example, there is a report on a specific genomic region closely related to diseases such as cancer, Crohn's disease, and schizophrenia. Cancer is a disease triggered by genomic abnormalities. A region to be subjected to sequence analysis differs depending on the tissue where cancer is developed, stage of the pathological condition, polymorphism which individuals essentially have, or the like. There is however a report on structural abnormalities such as deletion, insertion, and abnormality of copy number in a region extending from tensb to tens kb (Non-patent Document 1). In addition, there is a recent report that also in Chohn's disease which is an unexplained nonspecific inflammatory disease causing inflammatory or ulcers in the whole digestive tract region, deletion of abase region about 20k upstream of an immunity-related GTPase family M (immunity-related GTPase family, M) gene is closely related to the onset (Non-patent Document 2) of this disease. There is also a report on a plurality of gene loci related to the onset of schizophrenia (Non-patent Document 3).

Sequence analysis that limits a base region to be analyzed to a specific gene group, a gene group involved in related pathway, a genomic region including a region upstream or downstream of the related gene, "hot spot", that is, a base region having a high mutation rate per base, or the like is being recognized as markedly useful also from the standpoint of clinical application.

Different from such a sequence analysis that limits a base region to be analyzed, it is, in the conventional method, the common practice to extract, isolate, and elute a desired sequence fragment group by using a microparticle carrier having a probe for capturing a specific sequence fragment or a microarray having the above-mentioned probe immobilized onto a smooth substrate and thereby preparing a nucleic acid sample solution for analysis, and then conduct sequence analysis by using an existing sequencer. This means that a nucleic acid analysis device is manufactured by preparing a specific nucleic acid sample solution, amplifying using PCR, and immobilizing on a measuring substrate to be used for each sequencer and then sequence analysis is conducted using the sequencer. In these conventional methods, a step of extracting and isolating a specific sequence fragment and a series of pretreatment steps of a sample to be analyzed using a sequencer such as a step of introducing an adapter sequence into the end of a sample fragment through ligation and then conducting a PCR amplification reaction in an emulsion (oil droplet) or on a smooth substrate are completely separated from each other so that the conventional methods require a cumbersome wet treatment.

PRIOR ART DOCUMENTS

Patent Documents

[Patent Document 1] Japanese Patent No. 3897086
[Patent Document 2] US2003-0064400
[Patent Document 3] US2005-0250117

Non-Patent Documents

[Non-patent Document 1] Nature 2009, Vol. 458, pp. 719-724.
[Non-patent Document 2] Nature 2008, Vol. 447, pp. 661-678.
[Non-patent Document 3] Nature 2008, Vol. 455, pp. 919-923.
[Non-patent Document 4] Nanotechnology, 2007, Vol. 18, pp. 044017-044021.
[Non-patent Document 5] Genome Research 2008, Vol. 18, pp. 1051-1063.
[Non-patent Document 6] P.N.A.S. 2006, Vol. 103, pp. 19635-19640.

SUMMARY OF THE INVENTION

Problems that the Invention is to Solve

As a result of an intensive investigation on a method of conducting extraction of a specific nucleic acid fragment to be analyzed and parallel sequencing by using a successive and easy treatment, the present inventors have obtained the following finding.

It has been found that an analysis device necessary for single molecule sequencing can be manufactured easily and rapidly by using a microparticle having a size of 100 nm or less as a support carrier for extraction, using one molecule of a capture probe per microparticle carrier, and after capturing a target nucleic acid fragment, selectively immobilizing the microparticle serving as a support carrier onto a pad formed in advance on a smooth substrate.

When a plurality of kinds of capture probes is attached to one microparticle carrier, specific nucleic acid fragments captured should be cut and isolated after capturing. In addition, in order to immobilize a plurality of capture probe molecules of the same kind to one microparticle carrier, reactions should be conducted separately between the microparticle carrier and a tremendous number of capture probes, which is not practical. On the other hand, it has been found that when the number of capture probe molecules is set at one per microparticle carrier, only one immobilization reaction is necessary between a mixture liquid of the capture probe and the microparticle. It has further been found that preparation of a pad having a diameter equal to or less than the diameter of the microparticle facilitates immobilization of one microparticle to one pad and this finally makes it possible to manufacture a nucleic acid analysis device in which specific nucleic acid fragments have been immobilized one by one in lattice form on a smooth substrate, leading to completion of the present invention.

A preparation process of a single-molecule nucleic acid-loaded microparticle is disclosed in Patent Documents 2 and 3. Patent Document 2 discloses a process of modifying both ends of a double-stranded nucleic acid with biotin and digoxigenin, capturing a single-molecule nucleic acid-loaded magnetic microparticle by using a biotin-loaded magnetic microparticle and a digoxigenin antibody-loaded recovery microparticle, and finally isolating the recovery microparticle from the single-molecule nucleic acid-loaded magnetic microparticle under high-pH denaturing conditions, and collecting a single-molecule nucleic acid-loaded magnetic microparticle by using a magnet.

Patent Document 3 discloses three processes for preparing a single-molecule nucleic acid-loaded microparticle. Process (a): A double-stranded nucleic acid is modified at both ends thereof with oligo-dA and a capping oligonucleotide with a reactive group (such as biotin) and then hybridized with oligo-dT immobilized at a single molecule level to a top of binding agents provided with a predetermined distance on a substrate, followed by immobilization. Then, the microparticle with a binding site (such as avidin) and the reactive group are bound to each other. Finally, the oligo-dA is isolated from the oligo-dT under heating or high pH conditions to recover a single-molecule nucleic acid-loaded microparticle. Process (b): A single stranded nucleic acid having at an end thereof modified with biotin is prepared. It is reacted with an avidin-loaded microparticle to obtain a multimolecule single-stranded nucleic acid-loaded microparticle. The multimolecule nucleic acid-loaded microparticle is hybridized on a substrate on which complementary strand nucleic acids have been distributed. Moreover, many single-stranded nucleic acids which have failed to hybridize are digested by using exonuclease capable of digesting only single-stranded nucleic acids. Finally, a double-stranded nucleic acid is dissociated under heating or high pH conditions and a single-molecule nucleic acid-loaded microparticle is recovered. Process (c): An electric field is applied to a double-stranded nucleic acid and a microparticle bound to each other by a binding reaction and a single molecule nucleic acid-loaded microparticle is isolated from a multimolecule nucleic acid-loaded microparticle based on a difference in charged amount.

The process described in Patent Document 2 is a process of isolating a double-stranded nucleic acid under high pH denaturing conditions. In the process described above, however, re-hybridization occurs, which disturbs recovery of a single-molecule nucleic acid-loaded microparticle.

In the process (a) described in Patent Document 3, it is difficult to immobilize a single molecule of oligo-dT to the top of binding agents provided at certain intervals on a substrate. The process (b) has a problem that when the multimolecular single-stranded nucleic acid-loaded microparticle is hybridized on the substrate where complementary strand nucleic acids have been distributed and a reaction between the single-stranded nucleic acid and the complementary strand nucleic acid occurs in two or more pairs thereof, the recovered microparticle inevitably has two or more single-stranded nucleic acids. Also in the process (c), it is difficult to recover only a single-molecule nucleic acid-loaded microparticle through electrophoresis based on a difference in charged amount because a smear-like distribution disturbs clear isolation.

An object of the present invention is to provide a method of easily and rapidly analyzing the sequence information, among nucleic acid fragment samples, of only a specific nucleic acid fragment to be analyzed. In particular, an object of the invention is to provide a method of analyzing without using an amplification reaction such as PCR having a risk of involving mutation or having bias in population and requiring much time to prepare a sample. Another object is to provide a single-molecule probe nucleic acid-loaded microparticle and a preparation process thereof necessary for actualizing the above-mentioned method.

Means for Solving the Problems

According to the present invention, the base sequence information of a desired nucleic acid fragment group can be obtained by extracting, from nucleic acid fragment samples, only a specific target nucleic acid fragment to be subjected to sequence analysis without using an amplification reaction such as PCR and at the same time, immobilizing the target nucleic acid fragment on each of carriers onto a smooth substrate and then analyzing a fluorescent dye-labeled base to be incorporated during a sequencing reaction, for example, a complementary strand synthesis reaction. A single-molecule probe nucleic acid-loaded microparticle is used for extracting only the specific nucleic acid fragment to be subjected to sequence analysis. What is important in the preparation process of the single-molecule probe nucleic acid-loaded microparticle is a method of isolating a recovery microparticle from the single-molecule probe nucleic acid-loaded microparticle. The present invention has achieved efficient and stable recovery of an immobilizing microparticle by having, on the immobilizing microparticle, a hybridizing nucleic acid to be hybridized with a complementary strand nucleic acid on the recovery microparticle and a probe nucleic acid to be hybridized with a sample nucleic acid for analysis. FIG. 1 shows the respective constitutions of the immobilizing microparticle and the recovery microparticle. The term "probe nucleic acid" as used herein means a nucleic acid to be immobilized on the immobilizing microparticle in order to capture a sample nucleic acid. The term "hybridizing nucleic acid" means a nucleic acid to be immobilized on the immobilizing microparticle in order to be captured by the recovery microparticle. The term "complementary strand nucleic acid" means a nucleic acid to be hybridized with the hybridizing nucleic acid. Since on the immobilizing microparticle, the probe nucleic acid for capturing a sample nucleic acid and a hybridizing nucleic acid to be captured by the recovery microparticle are connected to each other and a binding site for binding to the immobilizing microparticle is present independently at a joint between the probe nucleic acid and the hybridizing nucleic acid, it becomes possible to easily recover immobilizing microparticles having many kinds of probe nucleic acids immobilized thereon by using the same recovery microparticle. When the binding between the immobilizing microparticle and the recovery microparticle is cut using a restriction enzyme digestion method, the hybridizing nucleic acid and the complementary strand nucleic acid are imparted with a restriction enzyme digestion site such as Xho I sequence. As a cutting method other than the restriction enzyme digestion method, a linker easily cleavable by a photoreaction or a chemical reaction with a chemical gent can be provided between the hybridizing nucleic acid and a binding site to the immobilizing microparticle.

Advantage of the Invention

The present invention makes it possible to easily and rapidly conduct sequence analysis of only a nucleic acid fragment to be analyzed without using an amplification reaction such as PCR by conducting an extraction step of the target nucleic acid fragment and an immobilizing step to a nucleic acid analysis device through a successive and simple treatment. In particular, sequence analysis can be conducted rapidly without a risk of single base substitution or bias in population due to the amplification reaction. Moreover, according to the present invention, single-molecule probe nucleic acid-loaded microparticles can be prepared efficiently and they can be immobilized onto a substrate while arranging them regularly with high density so that a nucleic acid sample can be analyzed with a high through-put.

BRIEF DESCRIPTION OF THE DRAWINGS

FIG. 1(a) is a schematic view showing a probe nucleic acid-loaded microparticle which is an intermediate product of a single-molecule probe nucleic acid-loaded microparticle according to one example of the present invention and FIG. 1(b) is a schematic view showing a recovery microparticle for recovering the probe nucleic acid-loaded microparticle.

FIG. 2 is a flow chart for describing the work flow of both the present invention and the prior art.

FIG. 3 is a diagram for describing one example of a step of capturing a target nucleic acid and a step of manufacturing a nucleic acid analysis device.

FIG. 4 is a diagram for describing one example of a nucleic acid analysis method using the nucleic acid analysis device.

FIG. 5 is a diagram for describing one example of the constitution of the nucleic acid analysis device.

FIG. 6 is a diagram for describing one example of a method of manufacturing the nucleic acid analysis device.

FIG. 7 is a schematic view for describing one example of a step in a preparation process of a single-molecule probe nucleic acid-loaded microparticle according to the present example.

FIG. 9 is a schematic view for describing one example of a nucleic acid analyzer using the nucleic acid analysis device.

FIG. 10 is a fluorescence image of a single-molecule nucleic acid-loaded microparticle immobilized onto a substrate and a waveform diagram of single-molecule bright spot.

MODES FOR CARRYING OUT THE INVENTION

Figure 1:
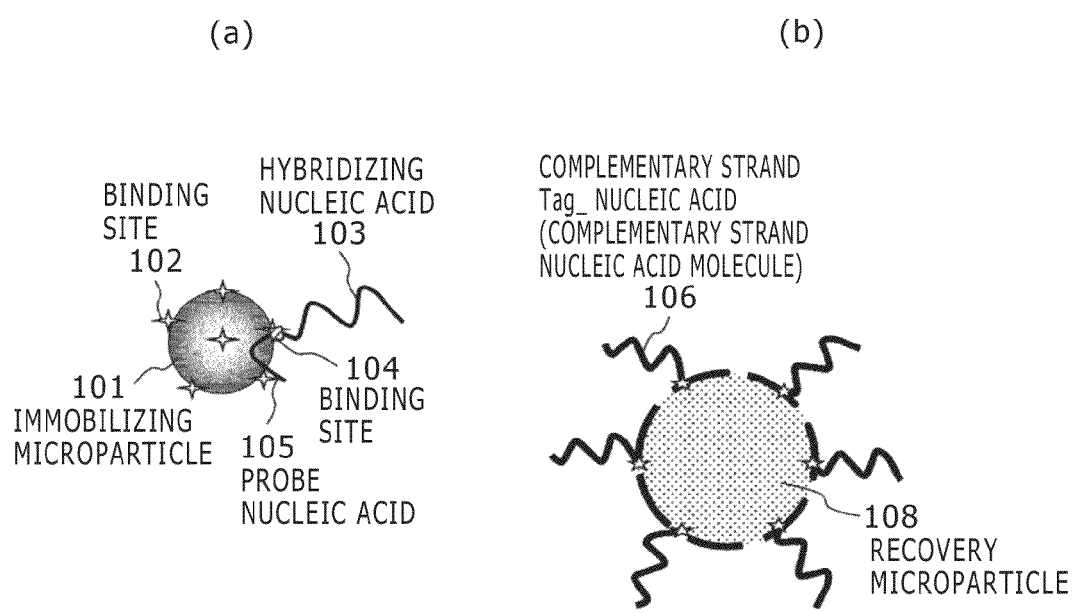
[FIG. 1]

In Example, there is disclosed a method of analyzing a nucleic acid including a step of extracting a specific nucleic acid group to be analyzed from nucleic acid samples by using a microparticle having a probe molecule capable of capturing the specific nucleic acid group to be analyzed, a step of immobilizing the microparticle onto a substrate, and a step of conducting sequence analysis of the nucleic acid group on the microparticle immobilized onto the substrate.

In Example, there is also disclosed the method of analyzing a nucleic acid, characterized in that the microparticle to be used in the step of extracting a nucleic acid group has one probe molecule per microparticle.

In Example, there is further disclosed the method of analyzing a nucleic acid, characterized in that the step of immobilizing the microparticle onto the substrate is a step of immobilizing the microparticle onto a bonding pad placed on the substrate.

In Example, there is further disclosed the method of analyzing a nucleic acid, characterized in that as the step of conducting sequence analysis of the specific nucleic acid group on the microparticle immobilized onto the substrate, the sequence information of the nucleic acid group is obtained by supplying a plurality of kinds of nucleotides having a fluorescent label onto the substrate to cause a synthesis reaction of a single molecule of a complementary strand to a single molecule of the nucleic acid sample on the substrate and measure the fluorescence intensity of a fluorescent dye which the incorporated nucleotide has.

In Example, there is further disclosed a method of manufacturing a nucleic acid analysis device including a step of extracting a specific nucleic acid group to be analyzed from nucleic acid samples by using a microparticle having a probe molecule capable of capturing the specific nucleic acid group to be analyzed and then, immobilizing the microparticle onto the substrate.

In Example, there is further disclosed the method of manufacturing a nucleic acid analysis device, characterized in that the number of the probe molecule per the microparticle is one.

In Example, there is further disclosed the method of manufacturing a nucleic acid analysis device, characterized in that a bonding pad is provided on a position of the substrate on which the microparticle is to be immobilized and the microparticle is immobilized onto the bonding pad.

In Example, there is further disclosed the method of manufacturing a nucleic acid analysis device, characterized in that the microparticle is immobilized regularly on the substrate.

In Example, there is further disclosed the method of manufacturing a nucleic acid analysis device, characterized in that in the method of manufacturing a nucleic acid analysis device, the microparticle is made of a material selected from polymer materials, semiconductors, and metals.

In Example, there is further disclosed a nucleic acid analyzer for acquiring base sequence information of a specific nucleic acid group to be analyzed, which analyzer is equipped with a nucleic acid analysis device having a substrate and a microparticle having a probe molecule and having extracted the specific nucleic acid group to be analyzed, a means for supplying the nucleic acid analysis device with a nucleotide having a fluorescent dye and a nucleic acid synthetase, a means for exposing the nucleic acid analysis device to light, and a light emission detection means for measuring fluorescence of the fluorescent dye incorporated in a nucleic acid strand as a result of a nucleic acid extension reaction caused by coexistence of the nucleotide and the nucleic acid synthetase on the nucleic acid analysis device.

In Example, there is further disclosed a nucleic acid analysis device having a substrate and a microparticle having a probe molecule and having extracted a specific nucleic acid group to be analyzed, characterized in that the microparticle has been immobilized onto the substrate.

In Example, there is further disclosed the nucleic acid analysis device, characterized in that the number of the probe molecule per the microparticle is one.

In Example, there is further disclosed the nucleic acid analysis device, characterized in that a bonding pad has been provided on the substrate and the microparticle has been immobilized on the bonding pad.

In Example, there is further disclosed the nucleic acid analysis device, characterized in that the microparticle has been immobilized regularly on the substrate.

In Example, there is further disclosed the nucleic acid analysis device, characterized in that in the nucleic acid analysis device, the microparticle is made of a material selected from polymer materials, semiconductors, and metals.

In Examples, there is further disclosed a probe nucleic acid-loaded microparticle which is an intermediate product of a single-molecule probe nucleic acid-loaded microparticle having an immobilizing microparticle onto which a probe nucleic acid for capturing a sample nucleic acid has been immobilized, characterized in that the probe nucleic acid and a hybridizing nucleic acid to be captured by a recovery microparticle for recovering the probe nucleic acid-loaded microparticle are each present as one molecule on the immobilizing microparticle.

In Example, there is further disclosed the probe nucleic acid-loaded microparticle which is an intermediate product of a single-molecule probe nucleic acid-loaded microparticle having an immobilizing microparticle on which a probe nucleic acid for capturing a sample nucleic acid has been immobilized, characterized in that the probe nucleic acid and the hybridizing nucleic acid to be captured by a recovery microparticle for recovering the probe nucleic acid-loaded microparticle have been connected to each other and at a joint between the probe nucleic acid and the hybridizing nucleic acid, a binding site for binding the joint to the immobilizing microparticle.

In Example, there is further disclosed a nucleic acid analysis method including a step of hybridizing a sample nucleic acid with the probe nucleic acid of the probe nucleic acid-loaded microparticle to analyze the presence of the immobilizing microparticle.

In Example, there is further disclosed a process for preparing a single-molecule probe nucleic acid-loaded microparticle, including a step of obtaining the probe nucleic acid-loaded microparticle having the probe nucleic acid and the hybridizing nucleic acid and a step of using the recovery microparticle having, bound thereto, a complementary strand nucleic acid molecule having a sequence of a complementary strand to the hybridizing nucleic acid to hybridize the complementary strand nucleic acid molecule with the hybridizing nucleic acid and thereby recovering the probe nucleic acid-loaded microparticle.

In Example, there is further disclosed a process for preparing single-molecule probe nucleic acid-loaded microparticles, wherein in a procedure of preparing the single-molecule probe nucleic acid-loaded microparticle, in the step of obtaining the probe nucleic acid-loaded microparticle as described in claim 2, the binding site present between the probe nucleic acid and the hybridizing nucleic acid has been modified with one compound selected from the group consisting of biotin, digoxigenin, dinitrophenol, and lectin in order to bind the binding site to the immobilizing microparticle.

In Example, there is also disclosed the process for preparing a single-molecule probe nucleic acid-loaded microparticle, characterized in that after recovery of the probe nucleic acid-loaded microparticle by using the recovery microparticle having, bound thereto, a complementary strand nucleic acid molecule having a sequence of a complementary strand to the hybridizing nucleic acid, the hybridizing nucleic acid is cut from the probe nucleic acid by using a method selected from the group consisting of digestion with a restriction enzyme, exposure to ultraviolet rays, digestion with protease, digestion with esterase, and cleavage of a disulfide bond by using DTT and β (beta)-mercaptoethanol, followed by digestion with a glycolytic enzyme to obtain the single-molecule probe nucleic acid-loaded microparticle.

In Example, there is further disclosed the process for preparing a single-molecule probe nucleic acid-loaded microparticle, characterized in that when digestion with a restriction enzyme is employed as the cutting method, the hybridizing nucleic acid and the complementary strand nucleic acid have a restriction enzyme digestion site such as Xho I sequence.

In Example, there is further disclosed the process for preparing a single-molecule probe nucleic acid-loaded microparticle, characterized in that when a method other than digestion with a restriction enzyme is employed as the cutting method, the hybridizing nucleic acid and biotin modification have therebetween one linker selected from the group consisting of a photocleavable linker, a peptide linker, an ester bond linker, a disulfide bond linker, and a sugar chain linker.

In Example, there is further disclosed the process for preparing a single-molecule probe nucleic acid-loaded microparticle, characterized in that the probe nucleic acid and the hybridizing nucleic acid have a strand length of 20 mer or greater.

The above-mentioned and other novel features and advantages of the present invention will hereinafter be described referring to the drawings. Some embodiments will be described specifically to facilitate a complete understanding of the invention but the invention is not limited to what is described herein.

EXAMPLE 1

Figure 2:
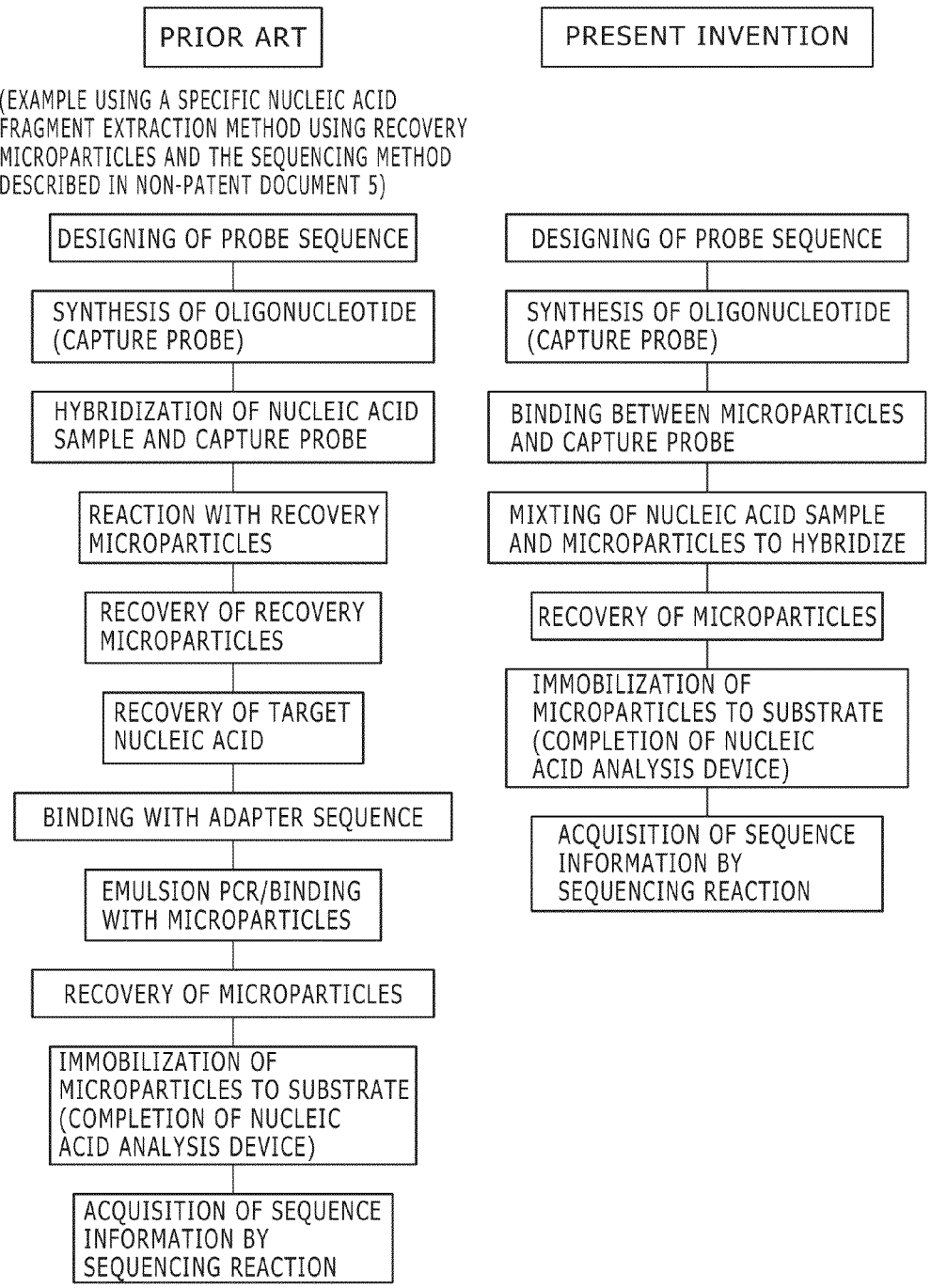
[FIG. 2]

Comparison in work flow between the invention and the prior art is shown in FIG. 2. First, the work flow of the prior art will be described.

First, in order to capture a nucleic acid fragment group to be analyzed, the sequence of a probe is determined in consideration of specificity and Tm (stability of a double strand) with the complementary sequence of it as a target. It is the common practice to preliminary modify with biotin in consideration of binding with recovery microparticles. After hybridization between a nucleic acid sample and the probe, recovery magnetic microparticles having a surface modified with avidin are put in a nucleic acid solution, followed by recovery by using a magnet. Then, high-temperature heat treatment at about 90° C. is conducted to separate the double strand into a single strand to obtain a target nucleic acid fragment. This is a step of extracting a nucleic acid fragment having a specific sequence.

Then, a pretreatment step of a sequencer sample is started. Here, the procedure and operation when the sequencing method (successive reaction system) described in Non-patent Document 5 which method has been used widely at present will be described. First, an adapter base sequence having from about 10 to 20 bases is added to the end of all the DNA sample fragments through a ligation reaction in order to give a primer sequence for PCR amplification reaction common to all the DNA sample fragments. Next, the DNA sample fragments, carrier microparticles, a DNA polymerase, and a primer are dispersed in an emulsion (oil droplet) to conduct the PCR amplification reaction and the microparticles are recovered to obtain microparticles having a PCR product immobilized onto the surface thereof. Next, the resulting microparticles are immobilized at random onto the surface of a slide glass to obtain a nucleic acid analysis device. In the sequencing method, the sequence information of the target nucleic acid fragment is obtained through a successive reaction system in which single base elongation, observation, and washing of four bases are repeated. A sequencing reaction is conducted by the PCR amplification reaction with microparticles each having about 1000 molecules having the same sequence immobilized thereon as a unit. Since the nucleic acid fragment extracted using the microparticles should be separated once and then immobilized to the microparticle carrier again, the sequence information cannot be obtained by conducting the steps from extraction to sequencing reaction in a successive and easy manner.

Next, the work flow of the invention will be described.

First, the sequence designing of a capture probe for capturing a nucleic acid fragment group to be analyzed is necessary. As a capturing method, hybridization can be used. When hybridization is used, a portion of a complementary sequence of a specific nucleic acid fragment to be subjected to sequence analysis can be used as the base sequence of the capture probe. At this time, it is preferred to sufficiently secure the specificity of the sequence and make uniform the Tm value in any combination of the capture probe nucleic acid and the nucleic acid fragment to be subjected to sequence analysis. By making uniform the stability of the double strand formed by hybridization, all the nucleic acid fragments to be subjected to sequence analysis can be immobilized onto a smooth substrate under reaction conditions after immobilization onto the substrate. For the sequence designing as described above, the method disclosed, for example, in Patent Document 1 can be employed.

Next, an oligonucleotide is synthesized based on the resulting designed sequence. Although no particular limitation is imposed on the base length of the oligonucleotide, it preferably falls within a range of from 20 to 100 bases in consideration of the practical Tm value. The end of the oligonucleotide is preferably modified with a functional group in consideration of the binding with the microparticles. For example, binding between the microparticle and the capture probe can be completed by preliminary modifying the end of the oligonucleotide with biotin, an amino group, or a sulfhydryl group and modifying the surface of the microparticle with avidin, succinimide, or maleimide, respectively. As the microparticles, those made of a material selected from polymer materials, semiconductors, and metals can be used. Although no particular limitation is imposed on the size of the microparticles, it is preferred to determine the microparticle size from the standpoints that handling for preventing aggregation is easy; when a bonding pad is used for immobilizing a microparticle onto a smooth substrate, the microparticle having a diameter at least equal to the diameter of the bonding pad is advantageous for limiting the number of the microparticles immobilized onto the pad to one; and when a label fluorescent dye of a matrix to be incorporated during a DNA elongation reaction is excited with an evanescent light by irradiating an excited light from the back surface of the smooth substrate, an excessively large microparticle increases the distance between the smooth substrate and the dye, leading to decrease in the intensity of the evanescent light and therefore decrease in fluorescent intensity of the dye. In consideration of these points, the diameter of the microparticle is preferably from about 10 nm to 100 nm. The method of immobilizing one molecule of the capture probe to one of the microparticles will be disclosed in Example 4. The microparticles having the capture probe immobilized thereto are poured in the nucleic acid sample and after hybridization, the resulting microparticles are recovered. The recovery can be achieved by centrifugal separation or by making use of a magnet when magnetic beads are used.

Next, the microparticles thus recovered are immobilized onto the surface of the smooth substrate to complete a nucleic acid analysis device. The immobilizing method will be disclosed specifically in Example 2.

Next, the sequence information of the nucleic acid fragment immobilized on the smooth substrate via the microparticles is acquired using a sequencing reaction. For the sequencing method, a nucleic acid analysis device obtained by immobilizing one molecule of the nucleic acid fragment to one of the bonding pads on the smooth substrate can be used so that the DNA elongation reaction can be observed at real time and compared with the successive method of repeating single base elongation, observation, and washing of only four bases, an observation time can be reduced and at the same time, a longer base length can be read.

Since the recovery microparticles having the target nucleic acid fragment captured thereon can be immobilized on the smooth substrate as are, a nucleic acid analysis device can be completed more rapidly and easily in less steps compared with the prior art. The sequence information can be acquired more rapidly because the number of the nucleic acid fragments to be captured is limited to one so that a real time system sequencing method can be used.

Figure 3:
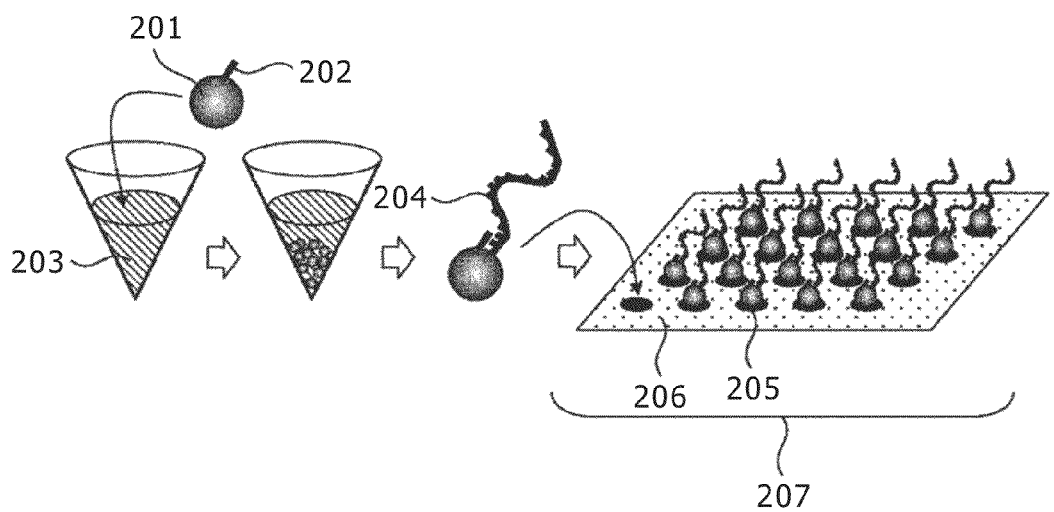
[FIG. 3]
Figure 4:
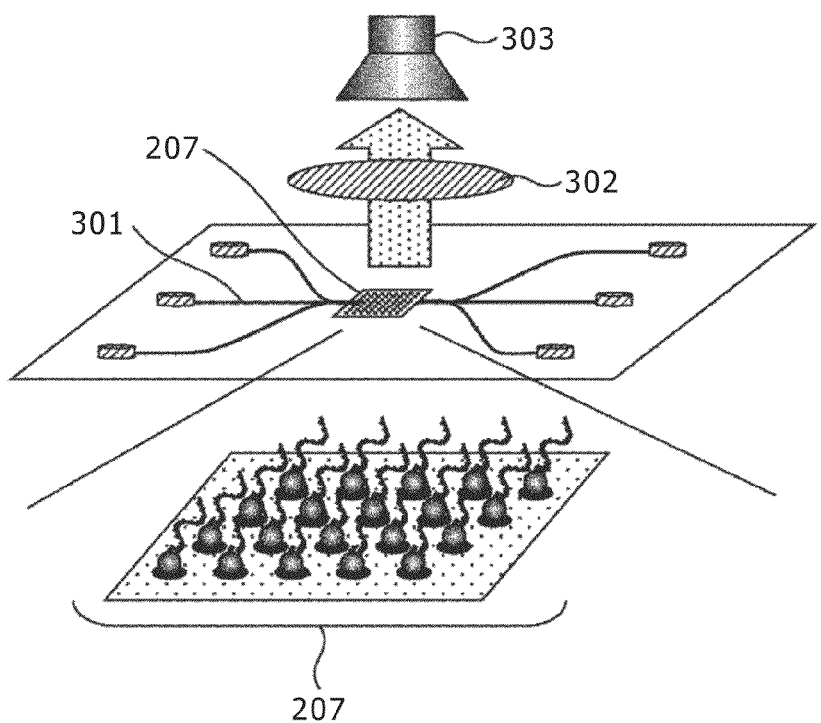
[FIG. 4]

Next, the nucleic acid analysis method, the nucleic acid analysis device, and the nucleic acid analyzer disclosed in the present Example will be described specifically referring to FIGS. 3 and 4. Only one molecule of a capture probe molecule 202 for capturing a specific nucleic acid fragment to be subjected to sequence analysis is bound to a microparticle 201 in advance. With regard to this one molecule immobilizing method, one example thereof will be disclosed in detail in Example 2. The microparticle 201 having the capture probe molecule 202 bound thereto is put in a nucleic acid sample solution 203. By separation after a reaction for a predetermined time, a specific target nucleic acid molecule 204 to be subjected to sequence analysis is captured. As a capturing method, a method using hybridization can be employed. As a method of separating and recovering the microparticle 201 after the target nucleic acid molecule 204 is captured, the microparticle can be recovered easily by filtering through a membrane having a size not permitting the passage of the microparticle 201 but permitting the passage of a nucleic acid sample which has not been captured. Centrifugal separation can also be used for it. The microparticle 201 may be made of a compound semiconductor, a metal, or a polymer in microparticle form. Microparticles made of a polymer material can have a uniform particle size and the particle size of it can be selected widely from tens of nm to several μm (micron meter). It is preferred to modify the surface of the microparticle by making use of the functional group of the polymer material, because an introduction amount of the functional group for an immobilizing reaction of the capture probe molecule 202 to be immobilized on the surface of the microparticle can be made uniform. In particular, when only one capture probe molecule 202 is immobilized on the surface of the microparticle, this modification is preferred because it achieves high reproducibility of an immobilization ratio.

The microparticles recovered are immobilized directly on a smooth substrate 206 having thereon a bonding pad 205 to complete a nucleic acid analysis device 207. A functional group capable of forming a bond with the functional group on the surface of the microparticle is introduced into the bonding pad 205 in advance. Details of it will be disclosed in Example 2. The diameter of the bonding pad 205 is made equal to or less than the diameter of the microparticle 201, which makes it possible to immobilize only one of the microparticles 201, that is, one molecule of the target nucleic acid molecule 204 to the bonding pad 205. By aligning a plurality of the bonding pads 205 in lattice form on the smooth substrate 206, it is possible to form the nucleic acid analysis device 207 in which the target nucleic acid molecules 204 to be analyzed are immobilized one by one on the smooth substrate 206 while being aligned in lattice form.

There may be some methods for detecting information relating to a nucleic acid sample from the nucleic acid analysis device of the present example, but a fluorescence detection method is preferred from the standpoint of sensitivity and convenience. The analysis method will next be described referring to FIG. 3 and FIG. 4. A microchannel 301 is formed on the nucleic acid analysis device 207, through which a DNA polymerase necessary for a DNA elongation reaction, a nucleotide labeled with a fluorescent dye, a buffer solution, and a washing solution can be supplied from the outside. The capture probe molecule 202 hybridized with the target nucleic acid molecule 204 works as a primer and causes a synthesis reaction of a complementary strand of the target nucleic acid molecule 204. Fluorescence of the fluorescent dye attached to the nucleotide to be incorporated in this synthesis reaction is collected using an optical system 302 including an objective lens and read using an image sensor 303, which makes it possible to measure respective elongation reactions on the bonding pads 205 independently and in parallel. For example, a so-called successive elongation reaction system in which supply of one of nucleotides, washing of an unreacted nucleotide, fluorescence observation, supply of a nucleotide different in kind from the above-mentioned one, and so on are conducted in repetition can be achieved easily. Base sequence information of a nucleic acid sample can be obtained by quenching the fluorescent dye after fluorescence observation or using a nucleotide labeled at a phosphoric acid site thereof with a fluorescent dye to cause a successive reaction. On the other hand, a so-called real time reaction system can be achieved by supplying four nucleotides having respectively different fluorescent dyes, causing a successive nucleic acid extension reaction without washing, and observing the fluorescence successively. In this case, when the nucleotide labeled at a phosphoric acid site thereof with a fluorescent dye is used, the phosphoric acid site is cut after the extension reaction so that base sequence information of the nucleic acid sample can be obtained by successively measuring the fluorescence without quenching it.

Thus, according to the invention, a nucleic acid analysis device can be formed by successively carrying out extraction, separation, and immobilization to a substrate of a specific nucleic acid fragment and by using this device, sequence analysis of individual nucleic acid fragments can be conducted in parallel.

EXAMPLE 2

Figure 5:
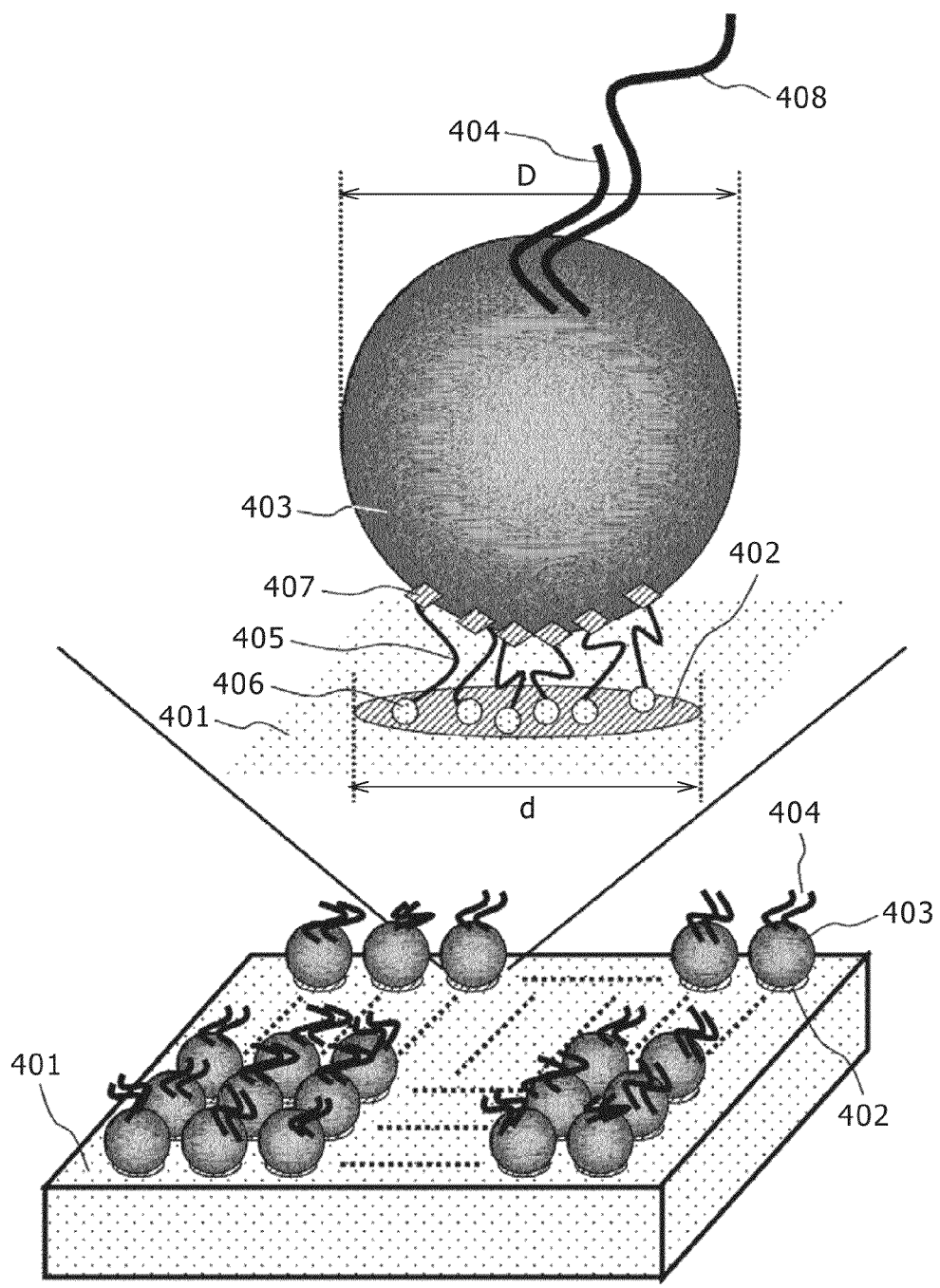
[FIG. 5]

One example of the constitution of the nucleic acid analysis device will next be described referring to FIG. 5. On a smooth substrate 401, bonding pads 402 are regularly formed, for example, in lattice form as shown in FIG. 5. The bonding pad 402 and a microparticle 403 are bound to each other via a linear molecule 405 through a chemical bond or chemical interaction. A functional group 406 at the end of the linear molecule 405 and the bonding pad 402 are preferably bound to each other through chemical interaction. At this time, the functional group 406 has preferably weak interaction with the smooth substrate 401 and strong interaction with the bonding pad 402. From such a viewpoint, quartz glass, sapphire, a silicon substrate, or the like can be used as the smooth substrate. The bonding pad 402 can be made of a material selected from gold, titanium, nickel, and aluminum. Although the functional group 406 should be selected in consideration of the combination between the smooth substrate 401 and the bonding pad 402, examples of it include a sulfhydryl group, an amino group, a carboxyl group, a phosphoric acid group, and an aldehyde group. The linear molecule 405 plays a role of binding the microparticle 403 to the bonding pad 402. No limitation is imposed on the length of it, but when it is a low molecular weight molecule, a straight-chain molecule having from about 3 to 20 carbon atoms is preferred. The terminal functional group 407 at the end of the linear molecule 405 provides the microparticle 403 with adhesion properties. When a high molecular weight molecule is used as the linear molecule 405, a molecule having a plurality of side chains, that is, a side chain having both a functional group 406 and a side chain having a functional group 407 can be used. As the microparticle 403, a metal microparticle or semiconductor microparticle can be used. For example, as a gold microparticle, that having a diameter of from 5 nm to 100 nm is commercially available so that it can be utilized. As the semiconductor microparticle, a compound semiconductor having a diameter of from 10 nm to 20 nm such as CdSe is commercially available so that it can be utilized. Functional groups usable as the functional group 407 differ, depending on the kind of the microparticle, but a sulfhydryl group, an amino group, and the like are suited for gold microparticles. When the semiconductor microparticle is used, a microparticle having a surface modified with streptavidin is commercially available and biotin can be used as the functional group 407. As a capture probe molecule 404 for capturing a target nucleic acid 408, a single strand of a nucleic acid molecule such as DNA or RNA can be used. The end of the nucleic acid molecule is modified in advance similar to the functional group 407 and is reacted with the microparticle 403. It is preferred that the number of the capture probe molecule 404 to be immobilized on one of the microparticles 403 is one. Also only one molecule of the target nucleic acid 408 is immobilized on the bonding pad 402.

In recognizing a probe by using simple fluorescence detection, the distance between probes is preferably about 1 μm (micron meter) in consideration of a diffraction limit. This means that the microparticle 403 having a size not greater than 1 μm (micron meter) is suited.

As a method of forming the bonding pad 402 on the smooth substrate 401, a thin-film process which has already been industrialized for semiconductors can be used. For example, it can be formed by vapor deposition and sputtering through a mask or by thin film formation by using vapor deposition and sputtering, followed by dry or wet etching. Regular arrangement of bonding pads can easily be achieved by using this thin film process. The distance between pads can be set freely, but when optical measurement is employed as a detection means, the distance is preferably 1 μm (micron meter) or greater in consideration of the diffraction limit of optical detection.

After formation of the bonding pad 402 on the smooth substrate 401, the linear molecule 405 for connecting the microparticle 403 and the bonding pad 402 is supplied and the linear molecule 405 is immobilized onto the bonding pad 402. At this time, it is effective to employ, prior to supply of the linear molecule 405, a method of reacting an upper portion of the smooth substrate 401 with a material having strong adhesive force with the smooth substrate 401 in order to prevent non-specific adsorption on the smooth substrate 401. For example, a silane coupling agent or the like can be used. Next, the microparticle which has captured the target nucleic acid molecule 408 with the capture probe molecule 404 is supplied onto the substrate and the microparticle 403 is immobilized onto the bonding pad 402 to complete the nucleic acid analysis device.

When the microparticle 403 is immobilized onto the bonding pad 402, there is a possibility of a plurality of the microparticles 403 being immobilized onto one of the bonding pads 402. Immobilization of a plurality of the microparticles makes it impossible to conduct precise analysis of the nucleic acid because data on nucleic acid fragments different in kind overlap with each other. One of the microparticles 403 should be immobilized onto one of the bonding pads 402. The present inventors therefore repeated an immobilization test under various conditions and carried out an intensive investigation. As a result, it has been found that one of the microparticles 403 can be immobilized onto one of the bonding pads 402 if the diameter d of the bonding pad 402 is smaller than the diameter D of the microparticle 403. This is presumed to occur because when the microparticle 403 equal to or greater than the bonding pad 402 is immobilized, an unreacted linear molecule is masked with the immobilizing microparticle and cannot react with another microparticle. The present inventors continued a further investigation. As a result, it has been revealed that when the microparticle 403 has an electric charge on the surface thereof, electrostatic repulsion works between the microparticles so that the number of the microparticles immobilized onto one of the bonding pads becomes one even when the diameter d of the bonding pad 402 is greater than the diameter D of the microparticle 403. It has therefore been elucidated that when the surface electric charge of the microparticle 403 is small and the electrostatic repulsion is weak, the diameter d of the bonding pad 402 is preferably smaller than the diameter D of the microparticle 403 and when the surface electric charge of the microparticle 403 is large and the electrostatic repulsion is strong, the diameter d of the bonding pad 402 is not necessarily smaller than the diameter D of the microparticle 403.

EXAMPLE 3

Figure 6:
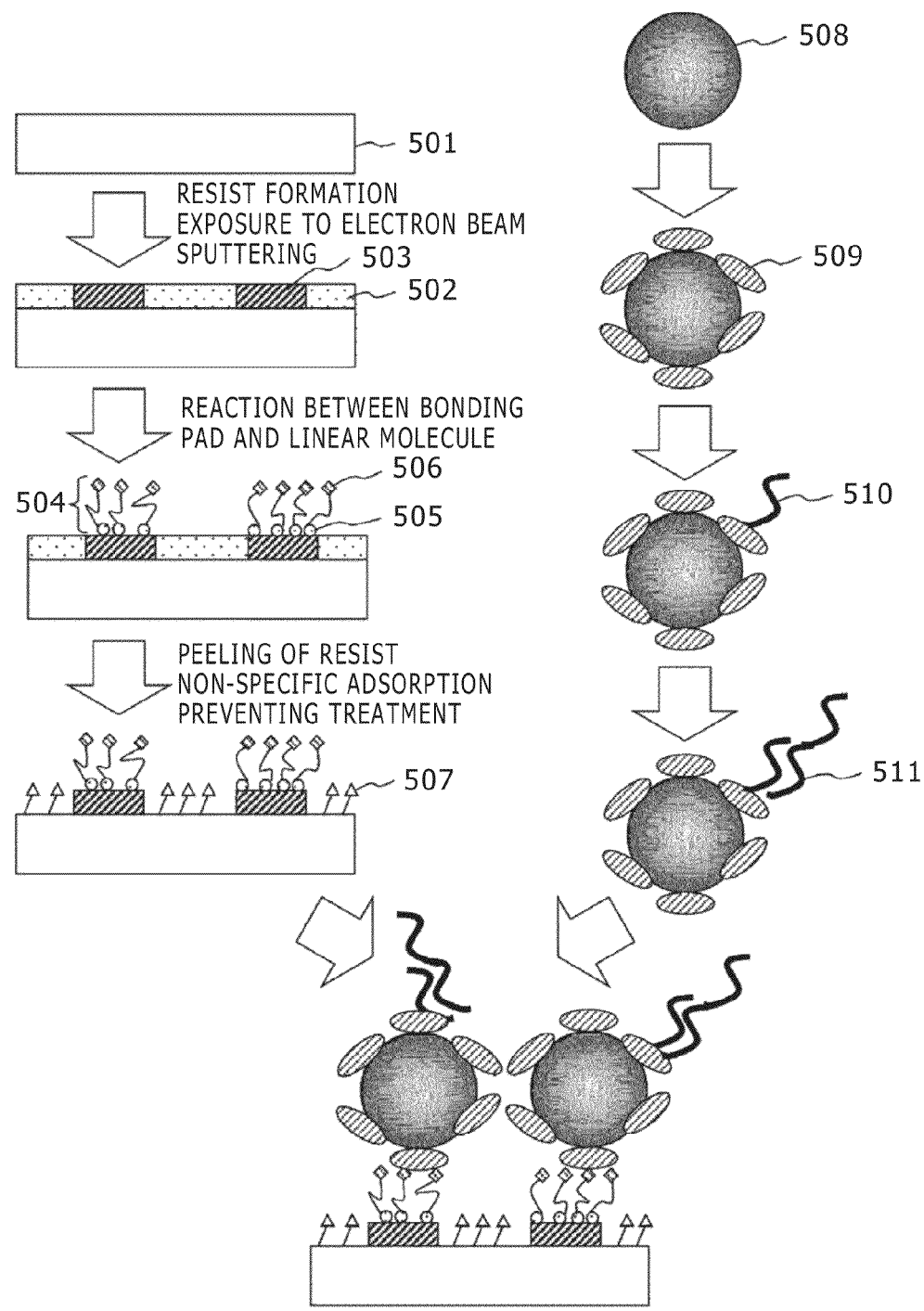
[FIG. 6]

One example of the manufacturing method of a nucleic acid analysis device will next be described referring to FIG. 6. An electron-beam positive resist 502 is applied onto a smooth support substrate 501 by using spin coating. As the smooth support substrate, a glass substrate, a sapphire substrate, a silicon substrate, or the like is used. When in the device, exposure to an excited light from the back surface of the substrate opposite to a surface on which microparticles have been placed is necessary, a quartz substrate or sapphire substrate excellent in light permeability may be used. Examples of the electron-beam positive resist include poly (methyl methacrylate) and "ZEP-520A" (product of Zeon Corporation). After alignment using a position of a marker on the substrate in advance, through-holes are made in a resist by electron-beam direct exposure. For example, a through-hole having a diameter of 15 nm is made. Although the pitch of the through-holes depends on the number of molecules of a nucleic acid analyzable by parallel processing, formation at a pitch of about 1 μm (micron meter) is suited s in consideration of ease of manufacture, high yield, and the number of molecules of a nucleic acid analyzable by parallel processing. The number of through-hole formation regions depends on the number of molecules of a nucleic acid analyzable by parallel processing but also depends largely on the position accuracy or position resolution of a detection device. For example, when reaction sites (bonding pads) are provided at a pitch of 1 μm (micron meter) and through-hole formation regions each have a size of 1 mm×1 mm, 1000 thousand reaction sites can be formed. After formation of the through-holes, a film is formed by sputtering by using a material constituting the bonding pad 503 such as gold, titanium, nickel, or aluminum. When a glass substrate or a sapphire substrate is used as the smooth support substrate and gold, aluminum, or nickel is used as a material of the bonding pad, a thin film of titanium or chromium is preferably inserted between the substrate material and the bonding pad material in order to reinforce adhesion of them. Next, a linear molecule 504 is reacted with the bonding pad 503. When the bonding pad 503 is made of gold, titanium, aluminum, or nickel, a sulfhydryl group, a phosphoric acid group, a phosphoric acid group, or a thiazole group is preferably used, respectively, as a functional group 505 at the end of the linear molecule. As a functional group 506 on the side opposite to the linear molecule, for example, biotin can be used. After the linear molecule is reacted with the bonding pad, the resist is peeled off. After the resist is peeled off, the surface of the smooth substrate except a portion thereof on which the bonding pad has been formed is subjected to non-specific adsorption inhibition treatment. In order to prevent adsorption to a fluorescent dye-labeled nucleotide, the surface of the smooth substrate is coated with a non-specific adsorption inhibition molecule 507 having a functional group negatively charged. For example, a non-specific adsorption inhibition effect can be produced by applying epoxy silane to the surface of the substrate by spin coating and after heat treatment, the surface is treated with a weak acid solution (having a pH of from about 5 to 6) to ring-open the epoxy group and introduce an OH group into the surface.

The surface of the microparticle 508 is preferably modified with avidin 509 in advance. When a gold or platinum microparticle is used, it can be easily modified with avidin by reacting the microparticle successively with aminothiol, biotin-succinimide ("NHS-Biotin", product of Pierce) and streptavidin. When a microparticle other than the gold or platinum one is used, it is heat-treated in an oxygen atmosphere to oxidize the surface thereof, followed by successive reaction with aminosilane, biotin-succinimide ("NHS-Biotin", product of Pierce), and streptavidin. In such a manner, the surface of the metal microparticle can easily be modified with avidin. When the microparticle used is a semiconductor microparticle, a commercially available microparticle can be used. For example, "Qdot(R) streptavidin conjugate" (trade name; product of Invitrogen) having a diameter of from 15 to 20 nm can be used. When oligonucleotide is used as a capture probe 510, that obtained by synthesis while modifying the end thereof with biotin can easily be immobilized onto the microparticle. The nucleic acid analysis device of the present example can be manufactured by putting the microparticle having the nucleic acid capture probe 510 immobilized thereto in a nucleic acid sample solution, capturing a target nucleic acid fragment 511 by hybridization, recovering the resulting microparticle, and reacting it with a bonding pad.

EXAMPLE 4

Specific examples of the single-molecule probe nucleic acid-loaded microparticle according to the present embodiment will next be described in detail.

As shown in FIG. 1(a), an immobilizing microparticle 101 for immobilizing thereon a single-molecule probe nucleic acid has, on the microparticle, a probe nucleic acid 105 for capturing a sample nucleic acid and a hybridizing nucleic acid 103 to be captured by a recovery microparticle 108 (FIG. 1(b)), each as a single molecule. A probe nucleic acid-loaded microparticle which is an intermediate product of a single-molecule probe nucleic acid-loaded microparticle is formed from the immobilizing microparticle 101 having the single-molecule probe nucleic acid 105 and the hybridizing nucleic acid 103.

The probe nucleic acid 105 and the hybridizing nucleic acid 103 are preferably connected to each other and a joint between the probe nucleic acid 105 and the hybridizing nucleic acid 103 (a description on the joint will be made in the below-described Example) has a binding site 104 for binding these nucleic acids to the immobilizing microparticle 101. This binding site 104 binds to a binding site 102 provided on the side of the immobilizing microparticle 101.

On the other hand, as shown in FIG. 1(b), a complementary strand nucleic acid 106 of the hybridizing nucleic acid 103 on the side of the immobilizing microparticle 101 has bound to the side of the recovery microparticle 108. This complementary strand nucleic acid 106 is hybridized with the hybridizing nucleic acid 103 to recover the single-molecule probe nucleic acid-loaded microparticle 101 by the recovery microparticle 108.

After recovery of the single-molecule probe nucleic acid-loaded microparticle, the immobilizing microparticle 101 and the recovery microparticle are separated from each other by using a cutting method such as digestion with a restriction enzyme to obtain a final single-molecule probe nucleic acid-loaded microparticle to be provided for a nucleic acid analysis device.

Figure 7:
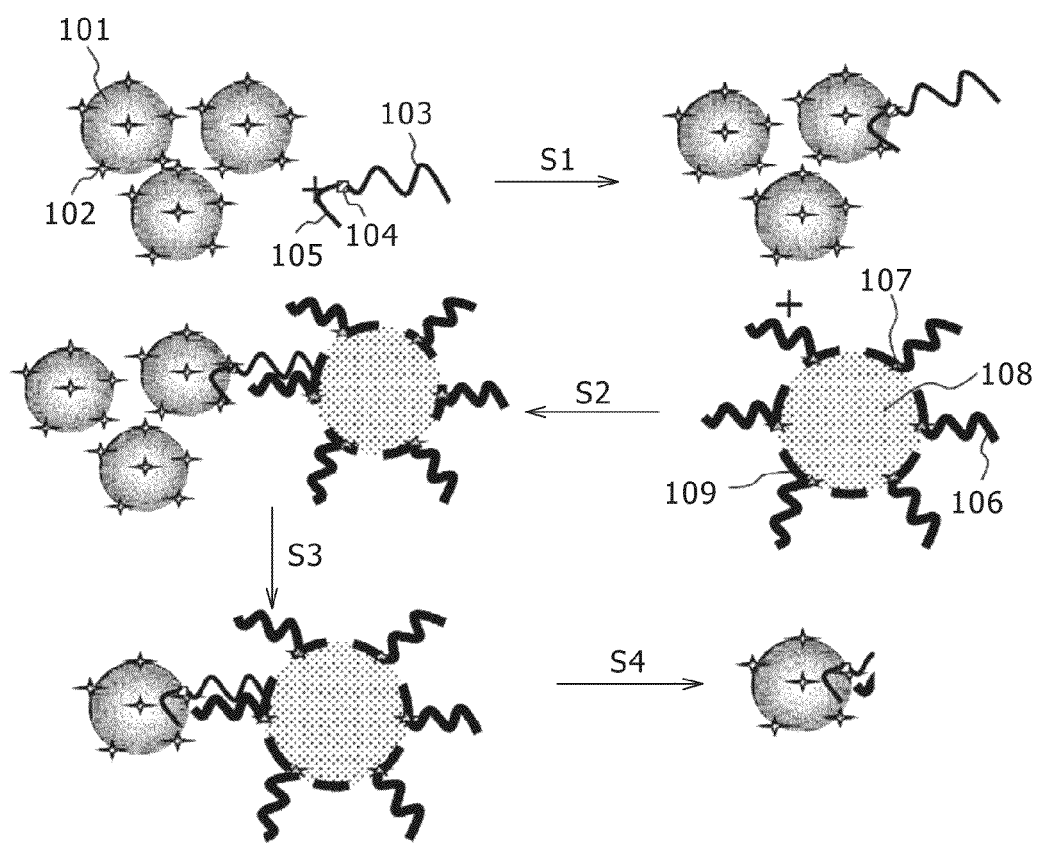
[FIG. 7]

FIG. 7 is a schematic view for describing one example of steps in a process for preparing a single-molecule probe nucleic acid-loaded microparticle. As shown in FIG. 7, a binding site 102 for capturing a probe nucleic acid molecule 105 has been bound to the surface of an immobilizing microparticle 101 in advance. For example, streptavidin can be used as the binding site 102. A commercially available streptavidin coated microparticle (product of Invitrogen) can be used as the immobilizing microparticle 101.

A probe nucleic acid molecule loaded-microparticle which is an intermediate product is obtained by immobilizing the probe nucleic acid molecule 105 for capturing a sample nucleic acid and a hybridizing nucleic acid 103 to be captured by a recovery microparticle onto an immobilizing microparticle 101 (Step 1). The probe nucleic acid molecule 105 and the hybridizing nucleic acid 103 are each in single-molecule form (one molecule). It is difficult to separately immobilize these nucleic acids on the immobilizing microparticle so that the 5'-side of the probe nucleic acid molecule is connected to the 3'-side of the hybridizing nucleic acid 103. A joint between them is modified with a binding site 104 for immobilizing to the immobilizing microparticle 101.

As the binding site 104, that easily binding to the binding site 102 on the surface of the immobilizing microparticle 101 is selected. For example, when streptavidin is selected as the binding site 102, biotin is used as the binding site 104.

The binding site 102 on the immobilizing microparticle 101 is reacted with the binding site 104 between the probe nucleic acid molecule 105 and the hybridizing nucleic acid in a reaction solution to immobilize (bind) the probe nucleic acid molecule 105 to the immobilizing microparticle 101. In order to immobilize one of the probe nucleic acid molecules 5 to one of the immobilizing microparticles 101, it is preferred to make the concentration of the probe nucleic acid molecules 105 in the reaction solution lower than the concentration of the immobilizing microparticles 101, because there is a possibility of the number of the probe nucleic acid molecules to be captured per the immobilizing microparticle 101 exceeding one when the probe nucleic acid molecules 105 are present more than the immobilizing microparticles 101. For example, when the reaction was conducted while increasing the number of the immobilizing microparticles 101 by 100 times the number of the probe nucleic acid molecules 105, about 99% of the immobilizing microparticles 101 did not capture the probe nucleic acid molecule 105 and about 1% of the immobilizing microparticles each captured one probe nucleic acid molecules 105. The above-mentioned results agree well with the prediction results based on the assumption of a Poisson distribution (the prediction results based on the assumption of a Poisson distribution are shown in Table 1).

When only the immobilizing microparticles 101 which have captured the probe nucleic acid molecule 105 are captured, 99.5% or more of the immobilizing microparticles 101 thus collected will be immobilizing microparticles 101 which have captured only one probe nucleic acid molecule 105.

TABLE 1

Prediction results based on the assumption of Poisson distribution

| | The number of probe nucleic acid molecules/the number of microparticles | | | | | | |
|---|---|---|---|---|---|---|---|
| | 0.002 | 0.01 | 0.02 | 0.1 | 0.5 | 1 | 2 |
| Percent of microparticles having one probe nucleic acid molecule bound thereto in immobilizing microparticles collected | 99.90% | 99.50% | 99.00% | 94.76% | 76.92% | 58.73% | 31.40% |

The binding site 102 and the binding site 104 are each either a covalently binding site or a non-covalently binding site. The non-covalently binding site means a site capable of specifically binding to a molecule having affinity with biotin, avidin, digoxigenin, dinitrophenol, glutathione, lectin, an antibody, or the like by immobilizing it to a microparticle. For example, biotin is capable of binding to a target nucleic acid biotinylated through a specific bond with avidin or a biotinylated polymer. The covalently binding site is one group selected from the class consisting of a carboxyl group (—COOH), a hydroxyl group (—OH), an alkoxycarbonyl group (—COOR1, wherein R1 represents a C1-10 alkyl group, a phenyl group, or a benzyl group), an amino group (—NH2), a thioxy group (—SH), and the like. Among them, the carboxyl group on the surface of the microparticle can be bound to an aminoalkyl group introduced into a nucleic acid in advance after being activated with an activating reagent such as 1-(3-diethylaminopropyl)-3-ethylcarbodiimide hydrochloride (EDC). The amino group on the surface of the microparticle can be converted into a carboxyl group by using a divalent reactive crosslinking reagent and bound to an aminoalkyl group introduced into a nucleic acid in advance or bound to phosphoric acid added to the end thereof. The hydroxyl group on the surface of the microparticle can be bound to an aminoalkyl group added to a nucleic acid after being activated with a tosyl group.

As the immobilizing microparticle 101 and the recovery microparticle 108, non-magnetic microparticles or magnetic particles can be used.

As the material of the non-magnetic microparticles, at least one material is selected from the group consisting of polystyrene, styrene-divinylbenzene, silica, borosilicate glass, soda lime glass, metals, semiconductors, minerals, quartz, and polymers. Examples of the non-magnetic microparticles usable here include Latex beads of SigMA-ALDRICH, FluoSpheres microspheres of Invitrogen, Dextran Nanospheres of microspheres-nanospheres, Polybead (trade mark) of Polysciences, Inc. and Polymer Microspheres of Thermo Fisher Scientific Inc. Examples of the magnetic microparticles usable here include Estapor (trade mark) of Merck Chime, S.A.S, Sera-Mag (trademark) and Magnetic SpeedBeads (trade mark) of Thermo Scientific Seradyn, BioMag (trade mark), Magnetic Microspheres, ProMag (trade name), and Highly Uniform Magnetic Microspheres of Polysciences, Inc., MagPrep (trade mark) of Merck4 Biosciences (Novagen), fluidMAG and SiMAG of chemicell, and Dynabeads of Invitrogen by life technologies.

The probe nucleic acid-loaded microparticle 101 having the above-mentioned constitution in the reaction solution is collected (recovered) through the recovery microparticle 108 (Steps S2 and S3).

The collecting method is as follows: the above-mentioned probe nucleic acid-loaded microparticle 101 is collected, for example, by binding the complementary strand nucleic acid molecule 106 to the magnetic recovery microparticle 108, hybridizing the resulting complementary strand nucleic acid molecule 106 with the hybridizing nucleic acid 103 of the probe nucleic acid-loaded microparticle 101, and then collecting the magnetic recovery microparticle 108 by using a magnet.

Described specifically, for the magnetic recovery microparticle 108, the complementary strand nucleic acid 106 having a strand sequence complementary to the end sequence of the hybridizing nucleic acid molecule 103 and having an end modified with a binding site 107 is prepared and the surface of the recovery microparticle 108 is coated in advance with a binding site 109 to be bound to the binding site 107. By using the magnetic recovery microparticle 108 thus prepared, the immobilizing microparticle 101 which has captured the single-molecule probe nucleic acid molecule 105 can be separated and collected in a yield as high as 99% or greater.

The probe nucleic acid-loaded microparticle 101 which will be a single-molecule probe nucleic acid-loaded microparticle can be isolated from the magnetic recovery microparticle 108 by using a cutting method (Step S4).

For example, a restriction enzyme digestion method can be employed for the isolation. The single-molecule probe nucleic acid-loaded microparticle 101 thus isolated can be immobilized to a predetermined fixing site on a smooth substrate by using the method (which will be described later) described in Example 2 and shown in FIG. 4. Thus, a nucleic acid analysis device having only one single-molecule probe nucleic acid molecule 105 of the present Example immobilized thereon can be manufactured.

When the immobilizing microparticle 101 exemplified in the present Example is a non-magnetic microparticle such as polystyrene, the recovery microparticle 108 is preferably a magnetic microparticle as described above.

When the immobilizing microparticle 101 is a magnetic microparticle, on the other hand, the recovery microparticle 108 is preferably a non-magnetic microparticle such as polystyrene. The recovery microparticle 108 has an average particle size of preferably from 100 to 10000 nm. When the recovery microparticle 108 is a magnetic microparticle, it can be collected by using a magnet. When the recovery microparticle 108 is a non-magnetic microparticle, a collection method making use of a difference in specific gravity can be used. For example, when the immobilizing microparticle 101 is a magnetic microparticle, it has a high specific gravity so that a polystyrene microparticle having a low specific gravity may be used as the recovery microparticle 108. For example, the magnetic immobilizing microparticle 101 bound to the recovery microparticle 108 can be recovered by mixing the recovery microparticle and the immobilizing microparticle in 60% glycerol, centrifuging the resulting mixture at 20,000×g for 3 minutes, and sucking the aqueous solution present in the upper layer.

When the immobilizing microparticle 101 is a magnetic microparticle, on the other hand, the recovery microparticle 108 is preferably a non-magnetic microparticle such as polystyrene. When the recovery microparticle 108 is a magnetic microparticle, it can be collected by using a magnet. When the recovery microparticle 108 is a non-magnetic microparticle, a collection method by making use of a difference in specific gravity can be used. For example, when the immobilizing microparticle 101 is a magnetic microparticle, it has a high specific gravity so that a polystyrene microparticle having a low specific gravity may be used as the recovery microparticle 108. For example, the magnetic immobilizing microparticle 101 bound to the recovery microparticle 108 can be recovered by mixing the recovery microparticle and the immobilizing microparticle in 60% glycerol, centrifuging the resulting mixture at 20,000×g for 3 minutes, and sucking the aqueous solution present in the upper layer.

Figure 8:
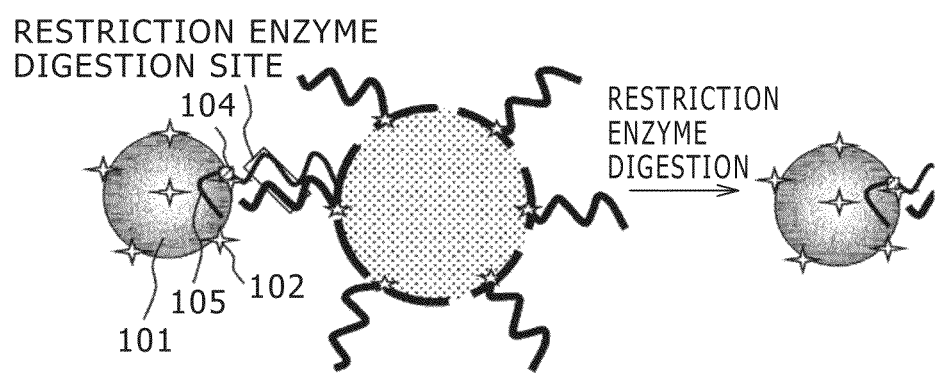
[FIG. 8]
FIG. 8 includes schematic views for showing specific examples (a) and (b) of a step, in the preparation process of a single-molecule nucleic acid-loaded microparticle, of recovering the single-molecule nucleic acid-loaded microparticle by using a recovery microparticle and then separating these microparticles (cutting method).
Figure 8:
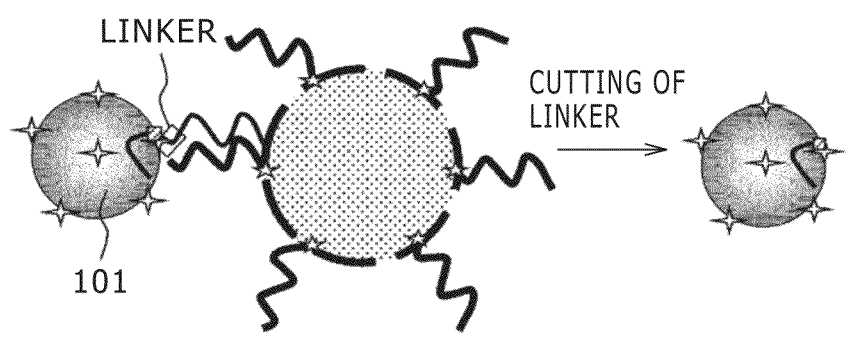

The recovery microparticle 108 and the immobilizing microparticle 101 can be separated from each other by using a cutting method. The cutting method usable here is a method of cutting the nucleic acids by using restriction enzyme digestion or UV exposure. When the restriction enzyme digestion method is used for cutting, the hybridizing nucleic acid 103 to be captured by the recovery microparticle and the complementary strand nucleic acid 106 on the recovery microparticle should have a restriction enzyme digestion site such as Xho I sequence. When a method other than the restriction enzyme digestion method is used, a linker easily cut by using an optical reaction or a chemical reaction using a chemical solution should be provided between the hybridizing nucleic acid 103 and the binding site 104. The cutting method and the kind of linkers are shown in FIG. 8 and Table 2.

TABLE 2

Kind of linkers and cutting method

| Kind of linkers | Cutting method |
| --- | --- |
| Photocleavable linker | Long-wavelength ultraviolet ray |
| Peptide linker | Protease |
| Ester bond linker | Esterase |
| Disulfide bond linker | DTT, β-mercaptoethanol |
| T-(EDTA) linker | Iron ion, DTT |
| Sugar chain linker | Glycolytic enzyme |

According to the cutting method, only the hybridizing nucleic acid 103 to be captured by the recovery microparticle is cut so that in a constitution having only the hybridizing nucleic acid 103 on the immobilizing microparticle 101, a sample nucleic acid for analysis cannot be captured. It is therefore preferred that also the probe nucleic acid 105 for capturing the sample nucleic acid is present on the immobilizing microparticle. The immobilizing microparticle has thereon both the probe nucleic acid for capturing the sample nucleic acid and the hybridizing nucleic acid to be captured by the recovery microparticle. Since it is difficult to immobilize them separately, the probe nucleic acid and the hybridizing nucleic acid connected to each other are preferably immobilized as one molecule on the immobilizing microparticle. The 3' end of the probe nucleic acid 105 is used for an extension reaction or the like so that the 3'-hydroxyl group of deoxyribose at the 3'-end is preferably in free form permitting binding of a phosphoric acid group of a nucleotide. When the binding site 104 for binding to the immobilizing microparticle is present not at a joint between the probe nucleic acid 105 and the hybridizing nucleic acid 103 but at the end, the binding site 104 to the immobilizing microparticle is present on the side of the hybridizing nucleic acid 103 and on the side of the probe nucleic acid 105. When the binding site 104 is present on the side of the hybridizing nucleic acid 103, cutting of the hybridizing nucleic acid 103 is accompanied by removal of the probe nucleic acid molecule 105 so that such a binding site cannot be used.

When the binding site 104 is present on the side of the probe nucleic acid 105 and the hybridizing nucleic acid 103 is cut, a portion of a linker or a portion of the complementary strand nucleic acid 106 is left so that the end of the probe nucleic acid cannot be used for the extension reaction. When the binding site 104 is present at a joint between the probe nucleic acid 105 and the hybridizing nucleic acid 103, there are two binding directions of the probe nucleic acid molecule and the hybridizing nucleic acid. When the 3'-side of the probe nucleic acid molecule 105 and the 5'-side of the hybridizing nucleic acid 103 are connected to each other, the 3'-side of the probe nucleic acid 105 cannot be used for the extension reaction because it is bound to the binding site 104. When the binding site 104 is attached between the 5'-side of the probe nucleic acid molecule 105 and the 3'-side of the hybridizing nucleic acid 103, the 3'-side of the probe nucleic acid molecule 105 can be used for the extension reaction because it is free. Therefore, the binding site 104 is attached between the 5'-side of the probe nucleic acid molecule 105 and the 3'-side of the hybridizing nucleic acid 103.

Labeling of a portion, which has remained after cutting of the hybridizing nucleic acid 103, with a fluorescent dye makes it possible to detect an immobilizing microparticle immobilized on the pad on the substrate after recovery of the single-molecule probe nucleic acid-loaded microparticle.

Specific examples of a photocleavable linker that can be cut with a long wavelength ultraviolet ray include linkers having a structure of an α (alpha)-substituted-2-nitrobenzyl group. Examples of the α (alpha) substituent include (i) phosphoramidites reactive with a hydroxyl group, (ii) N-hydroxysuccinimide carbonate reactive with an amino group, and (iii) halogens reactive with a thiol group. The photocleavable linker described above in (i) is, for example, PC Biotin Phosphoramidite, PC Amino Modifier Phosphoramidite, PC Spacer Phosphoramidite (each, trade name; product of Glen Research).

EXAMPLE 5

Figure 9:
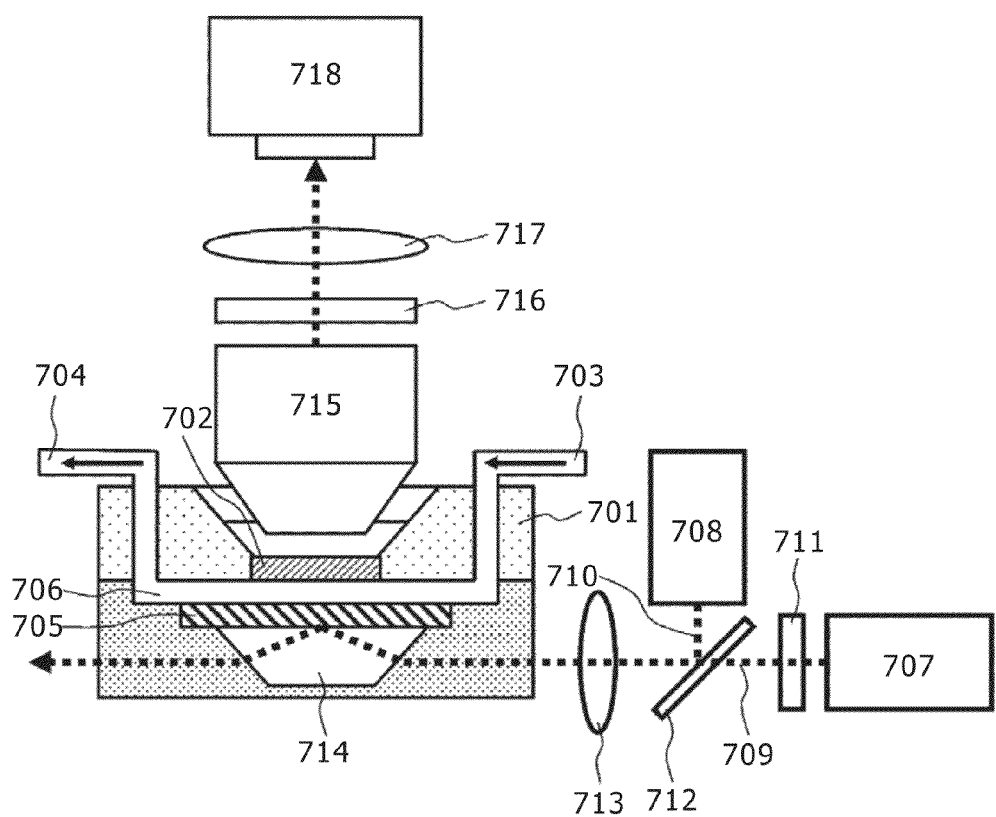
[FIG. 9]

In this Example, one example of a preferable constitution of a nucleic acid analyzer using a nucleic acid analysis device will be described referring to FIG. 9.

The nucleic acid analyzer of the present example is equipped with a means for supplying a nucleic acid analysis device with a nucleotide having a fluorescent dye and a nucleic acid synthetase, a means for exposing the nucleic acid analysis device to light, and an emission detection means for measuring the fluorescence of the fluorescent dye introduced into a nucleic acid strand as a result of a nucleic acid extension reaction caused by coexistence of the nucleotide and the nucleic acid synthetase on the nucleic acid analysis device. More specifically, the above-mentioned device 705 is placed in a reaction chamber comprised of a cover plate 701, a detection window 702, and an injection port 703 and an exhaust port 704 which are solution exchange ports. As the material of the cover plate 701 and the detection window 702, PDMS (polydimethylsiloxane) is used. The thickness of the detection window 702 is set at 0.17 mm. Laser lights 709 and 710 oscillated from a YAG laser light source (wavelength: 532 nm, output: 20 mW) 707 and a YAG laser light source (wavelength: 355 nm, output: 20 mW) 708, respectively, are regulated to have the same axis by, after circular polarization of only the laser light 709 with an λ/4 plate 711, using a dichroic mirror 712 (reflecting a light of 410 nm or less) and then collected by using a lens 713. Then, the device 705 is irradiated with them through a prism 714 at a critical angle or greater.

A description will next be made by using, as an example of the microparticle, a gold microparticle having a diameter of about 50 nm. In this case, laser irradiation generates localized surface plasmons in the gold microparticle present on the surface of the device 705 and a phosphor of a target substance captured by a DNA probe bound to the gold microparticle is present in a fluorescence enhancement site. The phosphor is excited by a laser light and a portion of the enforced fluorescence is output through the detection window 702. The fluorescence output from the detection window 702 becomes a parallel flux by an objective lens 715 (×60, NA 1.35, operating distance: 0.15 mm). The background light and excited light are blocked by an optical filter 716 and an image is formed on a two-dimensional CCD camera 18 through an imaging lens 717.

In a successive reaction system, as a fluorescent dye-labeled nucleotide, a nucleotide, as disclosed in Non-patent Document 6, obtained by introducing a 3'-O-allyl group serving as a protecting group into the 3' OH site of ribose and binding a fluorescent dye to the 5-position of pyrimidine or 7-position of purine through an allyl group can be used. The allyl group is cut by exposure to light (for example, wavelength: 355 nm) or by bringing into contact with palladium so that quenching of the dye and control of the extension reaction can be achieved simultaneously. Even in the successive reaction, it is not necessary to remove the unreacted nucleotide by washing. Moreover, since the washing step is not necessary, the extension reaction can be measured at a real time. In this case, the 3-O-allyl group is not required to be introduced as a protecting group into the 3' OH-position of ribose and it is only necessary to use a nucleotide coupled to a dye via a functional group cleavable by exposure to light (for example, wavelength: 355 nm).

The above-mentioned nucleic acid analyzer can also be applied even when as the microparticle, a semiconductor microparticle is used. For example, when Qdot (R) 565 conjugate (product of Invitrogen) is used as the semiconductor microparticle, excitation can be conducted fully by using a YAG laser light source (wavelength: 532 nm, output: 20 mW) 707. When this excitation energy is transferred to Alexa 633 (product of Invitrogen) that is not excited by a light of 532 nm, fluorescence is emitted. This means that the dye attached to an unreacted nucleotide is not excited and light emission occurs only after a nucleotide is captured by a DNA probe, comes close to the semiconductor microparticle, and energy transfer occurs. Thus, the captured nucleotide can be recognized by fluorescence measurement.

Figure 10:
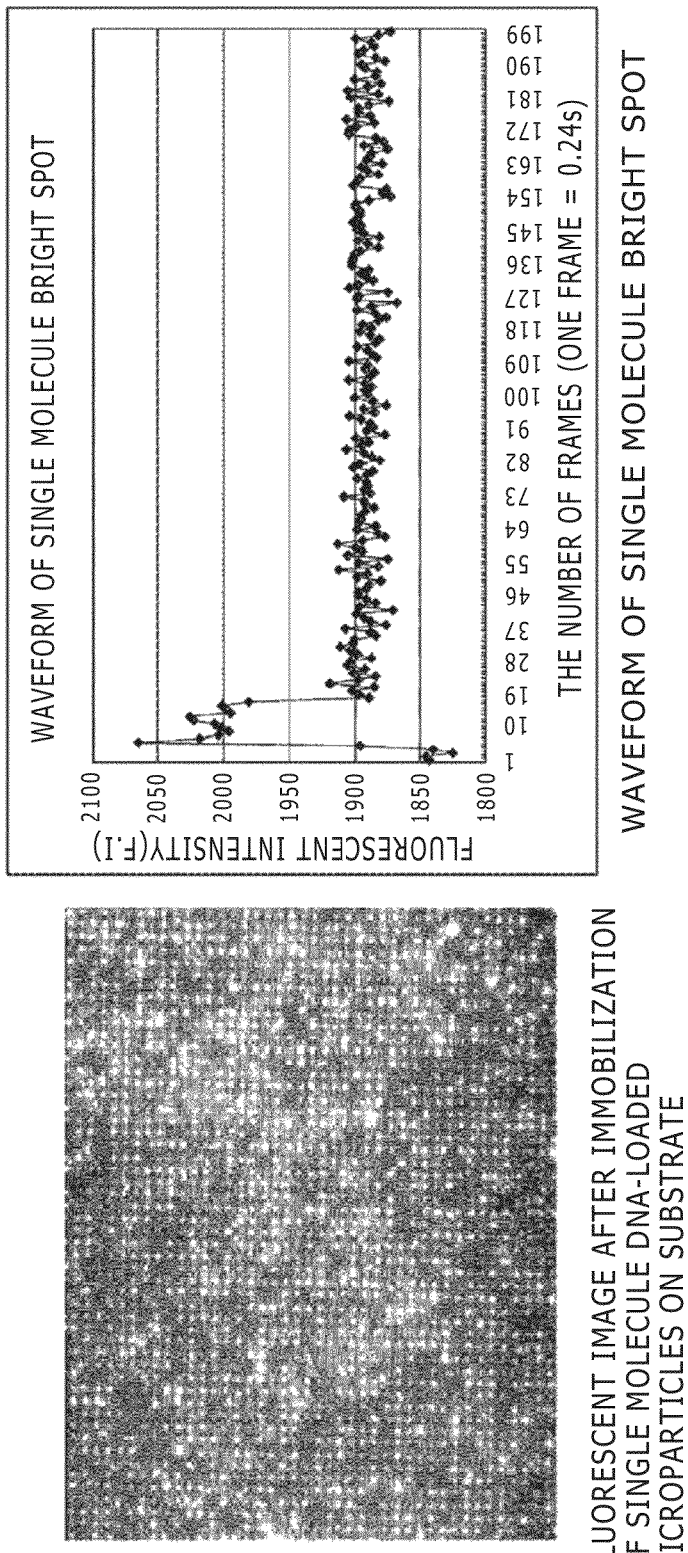
[FIG. 10]

FIG. 10 is a fluorescent image of a captured sample nucleic acid taken using the nucleic acid analyzer of the present embodiment after a single-molecule nucleic acid-loaded microparticle is immobilized onto a substrate and a waveform diagram of single-molecule bright spot.

As described above, since a nucleic acid analyzer is manufactured using the nucleic acid analysis device of the present embodiment, it is possible to omit the washing step, achieve a reduction in analysis time and simplification of the device and the analyzer, and to measure the extension reaction of a base not only by a successive reaction system but also at a real time. Thus, compared with the prior art, the invention produces a drastic improvement in throughput.

DESCRIPTION OF REFERENCE NUMERALS

101: Immobilizing microparticle, 102, 104, 107, 109: binding site, 103: hybridizing nucleic acid, 105: probe nucleic acid, 106: complementary strand nucleic acid, 108: recovery microparticle: 201: microparticle, 202: capture probe molecule, 203: nucleic acid sample solution, 204: target nucleic acid molecule, 205: bonding pad, 206: smooth substrate, 207: nucleic acid analysis device, 301: minute channel, 302: optical system, 303: image sensor, 401: smooth substrate, 402: bonding pad, 403: microparticle, 404: capture probe molecule, 405: linear molecule, 406, 407: functional group at the end of linear molecule, 408: target nucleic acid molecule, 501: smooth support substrate, 502: electron beam positive resist, 503: bonding pad, 504: linear molecule, 505, 506: functional group at the end of linear molecule, 507: nonspecific adsorption inhibition molecule, 508: microparticle, 509: Avidin, 510: capture probe molecule: 511, target nucleic acid molecule, 701: cover plate, 702: detection window, 703: injection port, 704: exhaust port, 705: device, 706: channel, 707, 708: YAG laser light source, 709, 710: laser light, 711: λ/4 plate, 712: dichroic mirror, 713; lens, 714: prism, 715: objective lens, 716: optical filter, 717: imaging lens, 718: two-dimensional CCD camera

The invention claimed is:

1. A probe nucleic acid-loaded microparticle which is an intermediate product of a single-molecule probe nucleic acid-loaded microparticle having an immobilizing microparticle onto which two kinds of nucleic acid have been immobilized, wherein one is a probe nucleic acid for capturing a sample nucleic acid and the other is a hybridizing nucleic acid which can be captured by a recovery microparticle for recovering the probe nucleic acid-loaded microparticle, wherein the probe nucleic acid and the hybridizing nucleic acid have been connected to each other and at a joint between the probe nucleic acid and the hybridizing nucleic acid, a binding site for binding the joint to the immobilizing microparticle is present, and the hybridizing nucleic acid has a restriction enzyme recognition sequence.

2. The probe nucleic acid-loaded microparticle according to claim 1, wherein a linker is provided between the hybridizing nucleic acid and the binding site, the linker able to be dissociated by using an optical reaction or a chemical reaction.

3. The probe nucleic acid-loaded microparticle according to claim 2, wherein one linker selected from the group consisting of a photocleavable linker, a peptide linker, an ester bond linker, a disulfide bond linker, and a sugar chain linker is provided.

4. A method of manufacturing a probe nucleic acid-loaded microparticle having an immobilizing microparticle onto which a probe nucleic acid for capturing a sample nucleic acid has been immobilized, comprising:

a step of obtaining the probe nucleic acid-loaded microparticle of claim 1, claim 2, or claim 3 having the probe acid and the hybridizing nucleic acid, a step of hybridizing a complementary strand nucleic acid having a sequence of a complementary strand to the hybridizing nucleic acid, by using the recovery microparticle having, bound to the complementary strand nucleic acid molecule, thereby recovering the probe nucleic acid-loaded microparticle, and a step of cutting the probe nucleic acid-loaded microparticle from the recovery microparticle.

5. A method of analyzing nucleic acid, comprising:

a step of extracting a specific nucleic acid group to be analyzed for analysis from nucleic acid sample by hybridizing a sample nucleic acid of the probe nucleic acid-loaded microparticle of claim 1, claim 2, or claim 3, a step of immobilizing the microparticle onto the substrate, and a step of conducting sequence analysis of the specific nucleic acid group on the microparticle immobilized on the substrate.

* * * * *